United States Patent [19]

Foreman

[11] Patent Number: 4,521,421
[45] Date of Patent: Jun. 4, 1985

[54] TREATMENT OF SEXUAL DYSFUNCTION

[75] Inventor: Mark M. Foreman, Indianapolis, Ind.

[73] Assignee: Eli Lilly and Company, Indianapolis, Ind.

[21] Appl. No.: 535,474

[22] Filed: Sep. 26, 1983

[51] Int. Cl.³ ............................................. A61K 31/505
[52] U.S. Cl. .................................................. 514/267
[58] Field of Search .......................... 544/250; 424/251

[56] References Cited

U.S. PATENT DOCUMENTS 3,793,324  2/1974  Penzer ................................. 544/250
4,198,415  4/1980  Kornfeld et al. ................... 424/258

OTHER PUBLICATIONS

Kaplan, *Disorders of Sexual Desire*, Brunner, Mazel Book Inc., N.Y., N.Y. 1979, only Appendix Table 1 attached.
Hollister, *Life Sciences*, 17, 661 (1975).
Spark et al., *Jama*, 243, 750 (1980).
Gessa and Tagliamonte, *Life Sciences*, 14, 425 (1974).
Malmnas, Acta. Physiologica Scandanavica, Suppl. 395, 47–68 and 69–128, (1973).
M. Da Prada et al., *Brain Research*, 57, 383, (1973).
Benassi-Benelli et al., *Arch. int. Pharmacodyn.*, 242, 241, (1979).
Falaschi et al., *Apomorphine and Other Dopaminomimetics, vol. 1, 117–121, (Gessa & Corsini Eds.–Raven Press, N.Y. 1981).*
Poggioli et al., *Riv. di Farm. & Terap., 9, 213, (1978).*
Ahlenius et al., *J. Neural Transmission*, 54, 165, (1982).
Tagliamonte et al., *Pharm. Biochem. Behav.*, 2, 257, (1974).
Ahlenius et al., *European J. Pharm.*, 64, 47, (1980).
Hlinat et al., *Psychopharm.*, 79, 231, (1983).
Silbergeld and Hruska, *Euro. J. Pharm.*, 58, 1, (1979).
Hyyppa et al., *Acta. Neurologia Scand.*, 46, Suppl. 43, p. 223, (1970).
Bommer et al., *Lancet*, 496, (1979).
Pierini and Nusimovich, *Archives of Andrology*, 6, 347, (1981).
Ambrosi et al., *Clinical Endocrinology*, 7, 417, (1977).
Pierini et al., *Int. J. Fertil.*, 24, 214, (1979).
Morales et al., *J. Urol.*, 128, 45, (1982).
Benkert, *Mod. Probl. Pharmacopsych.*, 15, 158, (1980).
Buffum, *J. Psychoactive Drugs*, 14, 5, 28–31, (1982).
March, *Drugs*, 17, 349, (1979).
Lees and Stern, *Lancet*, 246, 577, (1981).
Maneschi et al., *Hormone Res.*, 14, 79, (1981).
Perryman and Thorner, *J. Andrology*, 5, 233, (1981).
Rocco et al., *Arch. Andrology*, 10, 179, (1983).
Bairinos et al., *Psychoeneuroendocrinology*, 6, 341, (1981).
Kedia and Markland, *Urology*, 111, 569, (1975).
Kimura et al., *Andrologia*, 14, 341, (1982).
Hamburger-Bar and Rigter, *European J. Pharm.*, 32, 357, (1975).
Foreman and Moss, *Physiology & Behavior*, 22, 283, (1979).
Fuxe et al., *Subcellular Mechanisms in Reproductive Neuro-endocrinology*, Chapter 11, (Eds. Naftolin, Ryan and Davies, Elsevier, Amsterdam, The Netherlands, 1976).
Everitt and Fuxe, *Neuroscience Letters*, 4, 209, (1977).
Renshaw, *Mod. Probl. Pharmacopsych.*, 15, 145, (1980) (pp. 145 and 151 only supplied).

*Primary Examiner*—Leonard Schenkman
*Attorney, Agent, or Firm*—James L. Rowe; Arthur R. Whale

[57] ABSTRACT

Sexual dysfunction in mammals is treated with a trans-(±)- or trans-(−)-2-amino-4-permissibly-substituted-6-loweralkyl or allyl octahydropyrimido[4,5-g]quinoline or a pharmaceutically-acceptable acid addition salt thereof.

10 Claims, No Drawings

TREATMENT OF SEXUAL DYSFUNCTION

FIELD OF THE INVENTION

This invention relates to a method of treating sexual dysfunction with trans-(±)-2-amino-4-permissibly-substituted orally-6-alkyl-octahydropyrimido[4,5-g]quinolines and the trans-(−)-enantiomers.

BACKGROUND OF THE INVENTION

During recent years, sexual dysfunction in humans has become recognized as an increasingly important clinical entity. Such recognition is due in no small part to the pioneering work of William H. Masters and Virginia E. Johnson. In their books, *Human Sexual Response*, Little Brown and Company, Boston, 1966, and *Human Sexual Inadequacy*, Little Brown and Company, Boston, 1970, human sexual response is divided into four phases—excitement phase, plateau phase, orgasmic phase and resolution phase. Any disturbance or variation in this pattern is characterized by them (and others) as a sexual dysfunction.

A more recent, and preferable, categorization of human sexual response is that set forth in *Disorders of Sexual Desire*, Helen Singer Kaplan, M.D., Ph.D., Brunner Mazel Book Inc., New York, N.Y., 1979. Dr. Kaplan utilizes a triphasic concept of human sexuality—desire, excitement and orgasm. In males, the term "libido" has been used previously to describe the pre-excitement phase of sexual response. The excitement phase in both males and females is characterized by reflex vasodilatation of the genital blood vessels, resulting in an erection in males and by heightened coloring of the labia and lubrication in females. Disorders of the male excitement and desire phases are generally classified under the term impotence, inability to attain or maintain an erection, although some authors restrict the term to an erection disability alone. Dysfunction of the female excitement phase, inhibition of lubrication and swelling, is a relatively uncommon clinical syndrome.

Disorders of the orgasm phase in males includes premature or retarded ejaculation, and anorgasm in both males and females.

Sexual dysfunction, a disorder of one or more of the three phases of sexual response, has generally been treated by counseling. Drug treatment of such disorders has been rare. Masters and Johnson do record the treatment of elderly males with androgens, limited success only being attained.

Sexual dysfunction, besides being in part psychogenic in orgin, also includes dysfunctions brought about as a direct result of disease (diabetes) or as an indirect result; i.e., drugs used for treating hypertension in males frequently cause impotence. Kaplan, in Table 1, an appendix, lists the effect of drugs on the sexual response. Drugs are classed as sedative-hypnotics, including alcohol and barbiturates, antianxiety drugs, such as valium and librium, narcotics, such as morphine, the various antipsychotic agents, including phenothiazines and haldol, antidepressants, including the tricyclic antidepressants and the MAO inhibitors, stimulants such as cocaine, hallucinogens including LSD, miscellaneous CNS agents, including L-DOPA and parachlorophenylalanine, hormones, antihypertensives, antiadrenergic drugs, anticholinergic drugs, aphrodisiacs, etc. An examination of Table 1 indicates that a great majority of the drugs and drug types have no effect on the desire or excitement phase of the sexual response. A number of the drugs or drug types, however, are shown to cause impotence and thus may be a cause of sexual dysfunction. Cocaine and the aphrodisiacs alone seem to affect impotence in a positive manner. Many of the drugs in the table are said to cause impotence. It might also be noted that in the centrally acting anti-hypertensives, impotence is a major problem. L-DOPA, while having no affect on the excitement or orgasmic phases, is reported to increase desire in the elderly male patients afflicted with Parkinsonism. p-Chlorophenylalanine, an inhibitor of serotonin synthesis, is an aphrodisiac in rats but apparently has no effect on humans as will be set forth below.

It should also be noted that many of the drugs treat symptoms associated with sexual dysfunction and not the organic cause of the disease itself. For example, Kaplan reports a high degree of anxiety associated with sexual dysfunction in both males and females. An antianxiety drug would therefore be expected to have some positive effect in the treatment of such patients merely by alleviating the anxiety.

There is a physiologic basis for the treatment of both male and female sexual dysfunctions together since they have physiological responses in common. For example, testosterone is a libido hormone for both genders. In other words, lower testosterone levels might indicate a lowering of the desire phase in either sex. In addition, there are two centers in the spinal cord of humans associated with sexual arousal, one at $S_2$, $S_3$ and $S_4$ and a second at $T_{11}$, $C_{12}$, $L_1$ and $L_2$. These centers in the spinal cord become activated and cause the arteriols which invest the genitals to dilate. In addition, the reflex center for orgasm in males and females are located similarly in the sacral spinal cord. In both male and females there is a rhythmic contraction in certain striatal muscles during orgasm at the rate of 0.8 per second.

While the above discussion centers around the effect of drugs on sexual response in humans where the drugs were generally being taken for some other purpose, there are a series of studies on the effect of drugs on sexual performance where the drug was given for the sole purpose of aiding in the treatment of sexual dysfunction. According to Kaplan, page 80, "[t]he most common physiologic facts associated with HSD (hypoactive sexual desire) are depression and severe stress states, certain drugs and illnesses and low testosterone level". However, as will be seen from reference to the table 1 of Kaplan, antidepressant and antianxiety drugs are frequently associated with sexual dysfunction, particularly impotence in males, although they be helpful as an adjunct to psychotherapy. Kaplan reports that "phobic avoidance" can be treated with tricyclic antidepressants such as imipramine, amitryptilene and desimpramine or by MAO inhibitors such as diazepam. Here the medication is employed to protect the patient against panic attacks during sexual psychotherapy and does not "by itself" cure the symptom of sexual avoidance (which is primarily related to anticipatory anxiety) but creates conditions which makes psychotherapy more effective.

Hollister also reviewed the effect of drugs on sexual behavior in man in *Life Sciences*, 17, 661 (1975). The review is chiefly concerned with those drugs which decrease sexual activity including sympatholytics, ganglionic blocking agents, antipsychotics and lithium. The review also discusses at considerable length the use of illicit social drugs as sexual stimulants. For example, the enhancement of sexual activity by intravenous injection of large doses of amphetamine is in part attributed to its dopamine-mimetic activity. Cocaine apparently acts in the same way as does amphetamine. It is pointed out that marijuana, a drug of complex physiological action, though widely reported to enhance sexual behavior and intensity of orgasm, actually decreases plasma testosterone levels in chronic users.

Spark et al., *JAMA* 243, 750 (1980) review the problem of impotence. They report that, of 105 consecutive patients having impotence as a major presenting symptom, 37 of them had previously unsuspected disorders of the hypothalamic-pituitary-gonadal axis. Of these, 20 patients had hypogonadotropic-hypogonadism, 7 had hypergonadotropic-hypogonadism, 8 had hyperprolactinemia, and 2 had occult hyperthyroidism. The authors report that, once the specific defect was defined, appropriate therapy was instituted and potency restored in 33 patients. For the first group, appropriate therapy consisted of treatment with either testosterone enanthate or human chorionic gonadotropin. The hypergonadotropic group was also treated with testosterone enanthate injections. The patients with hyperprolactinemia were treated with bromocriptine to reduce prolactin levels. The fact that hyperprolactinemia (an excess of prolactin) in some men who are impotent has been recognized since 1977.

There have been many attempts to develop a rational basis for the drug treatment of sexual dysfunction. In this type of research, the role of various neurotransmitters in sexual behavior has been explored. Of the greatest relevance to this invention have been papers dealing with the roles of dopamine and serotonin or other brain monoamines in sexual behavior. For example, in 1974, Gessa and Tagliamonte writing in *Life Sciences*, 14, 425 (1974) reviewed the role of brain monoamines. They discussed the aphrodisiac effects of p-chlorophenylalanine in male animals and of L-DOPA in a number of Parkinson patients. The former selectively depletes brain serotonin and its aphrodisiac affect has been attributed to the removal of an inhibitory serotoninergic mechanism. They also report that sexual behavior of male rats had been found to be stimulated by elevating the level of brain dopamine or by stimulating brain dopamine receptors. The above findings led to a theory that male sexual behavior is reciprocally controlled by a central serotoninergic inhibitory and by a catecholaminergic stimulatory mechanism. After critically reviewing the evidence in animals and in man for the above theory, the authors believed that, although many problems remain to be clarified such as species differences, brain areas involved, possible cholinergic links, etc., such a theory has fascinating implications since it might offer a biochemical point of view for understanding some sexual disturbances in man.

Malmnas writing in *Acta. Physiologica Scandanavica*, Supplement 395 (1973) discusses, in two separate papers, the effect of monoamine precursors on the copulatory behavior of the male rat before and after impaired monoaminergic neurotransmission. In the first paper, pages 47–68, research directed to the effects of monoamine oxidase inhibitors (MAO) upon copulatory behavior is set forth, with the conclusion that these drugs suppressed such behavior. On the other hand, L-DOPA did not inhibit copulatory behavior when combined with pargyline, a monoamine oxidase inhibitor. The author concludes that testosterone-activated heterosexual copulatory behavior in the castrated male rat is inhibited by functionally increased central nervous serotonin content and facilitated by increased dopamine content. This paper represents one of the first to set forth the dual nature of sexual response depending apparently upon both serotonin and dopamine, as set forth in the previous paper. The second paper, pages 69–128, discusses the effect of two monoamine depletors, reserpine and tetrabenazine, on the copulatory behavior of castrated male rats activated by injections of testosterone. Both of the compounds decreased the copulatory response as did the catecholamine synthesis inhibitor, alpha-methyl-p-tyrosine. However, the serotonin synthesis inhibitor, p-chlorophenylalanine, discussed above as an aphrodisiac, facilitated the response. Again, it is the authors conclusion that testosterone-activated heterosexual copulatory behavior in the castrated male rat is facilitated by decreased serotonergic tone and inhibited by decreased dopaminergic tone.

Similar results were obtained by Da Prada et al writing in *Brain Research*, 57, 383 (1973). The authors found that administration of single doses of L-DOPA alone decreased 5HT (serotonin) in the central nervous system without increasing sexual activity. However, L-DOPA plus decarboxylase inhibitors after L-DOPA pretreatment did increase sexual activity.

Specific dopamine agonists other than L-DOPA have also been tested experimentally in rats for their effect on sexual behavior.

Benassi-Benelli et al., *Arch. int. Pharmacodyn*, 242, 241 (1979) injected both apomorphine and N-n-propyl-norapomorphine (apomorphine with a propyl group substituted for the methyl on the ring nitrogen) via the intraperitoneal route to adult male rats. The authors observed that such injections markedly increased episodes of penile erection. At very high doses, however, one and five milligrams per kilogram respectively, the natural occurrence of penile erection was suppressed. Haloperidol and sulpiride were found to prevent the sexual stimulant response to apomorphine and its n-propyl homologue. Domperidone, an inhibitor of extracerebral dopamine receptors, had no effect on this behavior. The authors also postulate that there are two sets of dopamine receptors in the brain, one responsible for the penile erection and the other for producing stereotypy, since doses of the two drugs which induce full stereotypy were relatively or totally ineffective in producing penile erection. In addition, no penile erection was observed when dopamine transmission was impaired by administration of neuroleptics, etc. The authors concluded that induction or inhibition of penile erection in rats may become an important screening test for drugs useful in the treatment of ejaculation disorders occurring in man.

Falaschi et al. *Apomorphine and Other Dopaminomimetics*, Vol. 1, 117–121 (Gessa and Corsini Eds.—Raven Press, N.Y. 1981) used dopamine receptor blockers to counter premature ejaculation in rats produced by the dopamine agonists, apomorphine and its N-n-phenyl analogue or L-DOPA plus a peripheral decarboxylase inhibitor.

Bromocriptine[2-bromo-α-ergocryptine] is another dopamine agonist whose effect in sexual behavior in rats has been investigated. Poggioli et al. *Riv. di Farm. & Terap.*, 9, 213 (1978) found that injections of bromocriptine induces a dose-dependent increase of penile erections, antagonized by haloperidol. Castration prevents the increase but pretreatment of the castrated rat with testosterone propionate restores the effect. The authors list several other drugs which are known to activate central dopaminergic receptors including p-chlorophenylalanine (p-CPA—a rat aphrodisiac without effect in humans), p-chloromethylamphetamine, d-amphetamine, apomorphine, amantidine, fenfluramine and L-DOPA.

Ahlenius et al. J. Neural Transmission, 54, 165 (1982) compared bromocriptine and pergolide, a drug currently on trial in Parkinsonism and known to have dopaminergic activity, for their effect on male rat sexual behavior. The authors found that pergolide, like lisuride (see below), produced a dose dependent decrease in the number of intromissions preceding ejaculation and shortened the ejaculation latency, but had no effect on any other component of the mating pattern. However, pergolide had less of an adverse effect on 5HT synthesis than did either of the other drugs. At the doses used, bromocriptine affected neither intromission frequency or ejaculatory latency but prolonged the postejaculatory interval. Both pergolide and lisuride ressembled the 5HT synthesis inhibitor, p-CPA, and produced their effects by activating presynaptic 5HT receptors. Dopamine receptor agonists, apomorphine, L-DOPA and amphetamine are said to have much weaker effects on male rats sexual behavior (see also Gessa and Paghietti et al Physiol. Behav., 20, 559 (1978). The authors conclude that an action on classic dopamine receptors is not responsible for effects produced by pergolide and lisuride.

On the other hand, Tagliamonte et al. Pharm. Biochem. Behav., 2, 257 (1974) demonstrated that apomorphine as well as L-DOPA improved the copulatory behavior in sexually sluggish male rats. The effect was prevented by haloperidol. The authors believe that their studies demonstrated that brain dopamine plays a stimulatory role in the copulatory behavior of male rats.

Lisuride, 6-methyl-8α-dimethylaminocarbonylamino-9-ergolene, has been referred to above. Ahlenius et al., European J. Pharm., 64, 47 (1980), found that treatment of male rats with lisuride decreased both the number of intromissions preceding ejaculation and the ejaculatory latency, indicating a positive effect on the sexual response. In addition, castrated sexually inexperienced rats treated with lisuride displayed a dose-dependent increase in complete heterosexual behavior. (Lisuride is 6-methyl-8-dimethylamino-carbonylamino-9-ergolene.) Lisuride is known to reduce brain 5HT as well as dopamine turnover and synthesis. Higher doses than those responsible for the above activities also increase brain noradrenaline. Effects of lisuride resemble those found with amphetamine or apomorphine; thus lisuride is a potent 5HT and DA receptor agonist. The authors observed that behavioral effects of lisuride, like those of p-chlorophenylalanine, may be due to impairment of brain 5HT neurotransmission but that lisuride also elicited symptoms of postsynaptic 5HT receptor activation.

Hlinat et al. writing in Psychopharm., 79, 231 (1983) also found that lisuride lowered the thresholds for sexual responses in animals to salient stimuli. The number of intromissions before ejaculation was decreased and the ejaculatory latency period was shortened. The authors drew no conclusions as to whether the perceived activity was due to dopaminergic or serotonergic actions or a combination of the two.

In research on effect on behavior generally by ergot-related drugs in rats, excluding sexual behavior, Silbergeld and Hruska, writing in Euro. J. Pharm., 58, 1 (1979) found that the "ergot drugs", lergotrile and bromocriptine at low doses both potentiated the "5-HT syndrome", a set of behaviors associated with increased serotonergic neurotransmission consequent to monoamine oxidase inhibition and tryptophan loading. At higher doses, the drugs antagonized the syndrome. The authors believed that it was possible that the drugs act to potentiate 5-HT through presynaptic dopaminergic pathways. On the other hand, the effects of the above and other drugs on the 5-HT syndrome may be through actions on serotonergic pathways. The possession of both serotonergic and dopaminergic properties by the drugs may be an advantage in Parkinsonism. Their evidence would contraindicate the use of a pure dopamine agonist in that disease, and would also indicate that these two ergot drugs, lergotrile and bromocriptine, would not be useful in sexual dysfunction if the dopamine agonist-serotonin antagonist hypothesis of Gessa and Tagliamonte (loc. cit.), among other authors discussed above, were correct.

In addition to the animal experiments discussed above, there is also a body of literature relating to the treatment of sexual dysfunction in males. Classes of patients in whom impotence is a common presenting side effect include diabetes, Parkinsonian patients and dialysis patients. Hyyppa et al., Acta. Neurologia Scand., 46, Supp. 43, page 223 (1970) interviewed Parkinsonian patients undergoing L-DOPA treatment concerning their sexual functioning. Ten males and three females had increased desire, and five of these increased sexual activity. The authors concluded that either dopamine or norepinephrine is a transmitter to the hypothalamus sexual behavior center.

Bommer et al., Lancet, 496 (1979) studied the effect of bromocriptine on sexual function in male hemodialysis patients. The authors found that a dose of 2.5 mg. of bromocriptine twice a day decreased plasma prolactin concentration and improved sexual function. Side effects, particularly hypotension, were common at the dosage used.

Pierini and Nusimovich, Archives of Andrology, 6, 347 (1981) carried out a double blind study with placebo and dopaminergic agents in 100 patients suffering from male diabetic sexual impotence. It is their conclusion that sexual activity improved in 50% of patients administered 3,4-dihydroxyphenylalanine (dopa) compared to 10% in the placebo group. Among patients given bromocriptine, 20% reported improved sexual function compared to none in the placebo group. The authors attribute the difference between the effects of L-DOPA and bromocriptine to the presence of two dopamine receptors—inhibitory and excitatory—in the brain and that the stimulation of selective receptors by different dopaminergic drugs explain the discrepancies. (This view that there are two types of dopamine receptors in the brain is not shared by all workers in the field—see, for example, Scatton, J. Pharm. Exper. Therap., 220, 197 (1982).)

The use of bromocriptine in treating sexual impotence in diabetics has been alluded to above. Ambrosi et al. Clinical Endocrinology, 7, 417 (1977) treated 47 non-diabetic male patients suffering from impotence. In a double blind study, no appreciable difference was found in hormonal patterns between bromocriptine and placebo but, as far as sexual function was concerned, good results were obtained in 52% of the treated cases and 44% of those given placebo.

Pierini et al., *Int. J. Fertil.*, 24, 214 (1979) also studied the effect of bromocriptine on the prolactin and testosterone levels in 20 males suffering from impotency of unknown origin. Ten showed an improvement in sexual potency and, of these, six were suffering from hyperprolactinemia. Ten showed no effect. The patients in whom bromocriptine produced improved sexual function all had low levels of testosterone whereas those in whom bromocriptine had no effect had normal testosterone levels.

Finally, Morales et al. *J. Urol.*, 128, 45 (1982) had some success in treating impotent males with an alpha-adrenergic blocker, yohimbine.

Benkert *Mod. Probl. Pharmacopsych.*, 15, 158 (1980) reviews the pharmacotherapy of sexual impotence in the male. He concludes (page 163) that lowering of serotonin increases sexual behavior (serotonin is an inhibitor of sexual behavior) but that evidence as to the effect of increasing dopamine, as by the administration of a dopamine agonist, on sexual behavior is contradictory. He concludes that clinical results do not justify therapeutic use of L-DOPA to treat impotence. In reviewing the therapeutic efficacy of bromocriptine, a dopamine agonist, he mentions a study carried out under his auspices with ten impotent males. Only three of ten showed a therapeutic effect and this number did not exceed the expected placebo effect. In other words, the positive results were not statistically significant. p-CPA, p-chloroamphetamine and methysergide also gave results indistinguishable from controls. The author concludes with the statement that "[t]here is no pharmacotherapy for sexual impotence . . . ".

The above drugs are also reviewed by Buffum, *J. Psychoactive Drugs*, 14, 5, 28–31 (1982). In a section of the review dedicated to drug enhancement of sexuality, he concludes that the observed effects of bromocriptine in impotent males are due to its direct effects on pituitary lactotrophs to inhibit prolactin secretion, activation of the dopamine receptors of the lactotrophs and action on hypothalamic centers. Only males with hypoganadotrophic, hypogonadism and prolactinemia can expect to benefit from bromocriptine. The actions of L-DOPA, p-CPA, etc. are also reviewed.

March, *Drugs*, 17, 349 (1979) also concludes that bromocritpine is of little value in the treatment of impotence unless hyperprolactinemia is a component of the disease. In many of such men successfully treated, testosterone levels were normal.

Lees and Stern, *Lancet*, 246, 577 (1981) reported that two of ten Parkinsonian patients treated with pergolide experienced spontaneous penile erections.

The presence of prolactinemia in impotent males has been alluded to above. Maneschi et al. *Hormone Res.*, 14, 79 (1981) measured 24 hour prolactin levels in diabetic patients. Levels were similar in impotent and sexually normal males, suggesting that diabetic impotence is not mediated by prolactin secretion.

Perryman and Thorner, however, writing in *J. Andrology*, 5, 233 (1981) found that 90% of prolactinemic males are impotent. Treatment of such impotent males with bromocriptine resulted in improved libido and potency accompanied by a fall in prolactin levels.

Rocco et al. *Arch. Andrology*, 10, 179 (1983) conclude that, as to impotence in hyperprolactinemia, with hyperprolactinemia, androgen levels are reduced and sexual behavior is directly inhibited, and that a decreased central dopamine function could affect both hyperprolactinemia and impotence.

Contrawise, Bairinos et al. *Psychoeneuroendocrinology*, 6, 341 (1981) conclude from a study of 57 males with inadequate sexual function that prolactin levels are normal and testosterone levels not reduced in otherwise healthy impotent men and that sexual dysfunction in patients with a pituitary adenoma is not necessarily associated with abnormal prolactin secretion. In these males, desire was normal but there were erection difficulties.

A majority of the above studies have centered on the desire and excitement phases of the sexual response. Certain aspects of orgasmic dysfunction have also been studied (besides the use of serotonergic or dopamine antagonist drugs in treating premature ejaculation alluded to previously).

Kedia and Markland, *Urology*, 111, 569 (1975) found that alpha-blockers can interfere with one phase of ejaculation and may be a cause of infertility in those males on a drug of this type. The suggestion was made that an alpha-blocker might be a reversible male contraceptive.

Kimura et al. *Andrologia*, 14, 341 (1982) studied the relationship of various monoaminergic systems in the brain to ejaculation. They concluded that ejaculation is activated by the dopaminergic system in the brain.

There are also studies of the effect of various drugs, particularly dopaminergic drugs, on female sexual behavior.

Hamburger-Bar and Rigter, *European J. Pharm.*, 32, 357 (1975) found that apomorphine increased the lordosis (lordosis is a precopulatory response) in response to a mounting male in spayed female rats who had been estrogen and progesterone-primed. The authors postulated a role for dopamine in controlling sexual receptivity.

Foreman and Moss, *Physiology & Behavior*, 22, 283 (1979), investigated the role of hypothalamic dopaminergic receptors in the control of lordosis behavior in the female rat. The authors concluded that hypothalamic dopaminergic receptor reactivation may contribute to the stimulatory effect of luteinizing hormone-releasing hormone upon lordotic behavior in female rats.

Fuxe et al., in reviewing the role of neurotransmitters and hypothalamic hormones on, among other functions, sexual behavior, in Subcellular Mechanisms in Reproductive Neuroendocrinology, Chapter 11, (Ed. Naftolin, Ryan and Davies, Elsevier, Amsterdam, The Netherlands, 1976) at page 230, state that some studies from their laboratories indicate that dopamine pathways inhibit sexual behavior. However, apomorphine and another dopamine receptor agonist, enhance sexual behavior at lower doses in the ovariectomized rat. It is the authors conclusion that dopamine inhibits sexual behavior (page 232).

The conclusion by Fuxe et al. is based on a paper by Everitt and Fuxe, *Neuroscience Letters*, 4, 209 (1977). Particular attention is called to the graph on page 210 wherein the fall off of activity with the increasing dose of various dopamine agonists in ovariectomized estrongen-primed rats is presented. The authors conclude that dopamine has an inhibitory role in the hormonal control of sexual receptivity in the rat.

Finally, Renshaw, in a review of the effect of various drugs on female sexuality in *Mod. Probl. Pharmacopsych.*, 15, 145 (1980) (pages 145 and 151 only supplied), discusses bromocriptine. Although the drug was touted as a "female aphrodisiac", the author urges caution in its use. The scientific basis for this report is not available.

A group of trans-(±) and trans-(−)-2-amino-4-permissibly-substituted (Cl, Br or CH$_3$)-6-alkyl or allyl-5,5a,-6,7,8,9,9a,10-octahydropyrimido[4,5-g]quinolines are disclosed and claimed in the copending application of Nichols and Kornfeld, Ser. No. 535,503, filed this even day.

SUMMARY OF THE INVENTION

This invention provides a method of potentiating sexual behavior or of treating sexual dysfunction in mammals which comprises administering to a mammal suffering from a sexual dysfunction or needing sexual potentiation and in need of treatment a dose of a compound of formula I [trans-(±)] or II to alleviate a sexual dysfunction or to potentiate sexual behavior in mammals

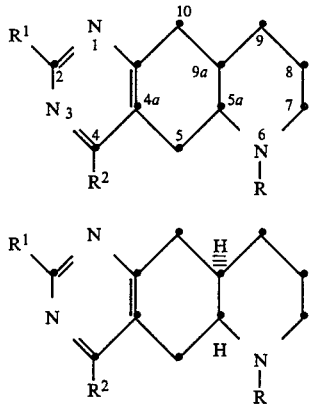

wherein R is C$_1$–C$_3$ alkyl or allyl, R$^1$ is NH$_2$, NHR$^3$, NR$^4$R$^5$ and R$^2$ is H, CH$_3$, Cl or Br wherein R$^3$ is methyl, ethyl or n-propyl, C$_1$–C$_3$ alkyl-CO, phenyl-CO or substituted phenyl-CO wherein said substituents are 1 or 2 members of the group: Cl, F, Br, CH$_3$, C$_2$H$_5$, CH$_3$O, C$_2$H$_5$O and CF$_3$; R$^4$ and R$^5$ are individually methyl, ethyl or n-propyl and pharmaceutically-acceptable acid addition salts thereof. A second embodiment of this invention comprises the treatment of impotence in male mammals by the administration thereto of a drug according to I or II in a dose sufficient to restore potency.

Compounds represented by I have two asymmetric centers; the bridgehead carbons C-5a and C-9a. The two racemates in question are the trans-(±)-racemate—trans-(±)-2-amino-6-alkyl or allyl-4-permissibly-substituted-5,5a,6,7,8,9,9a,10-octahydropyrimido[4,5-g]quinoline—and the corresponding cis-(±)-racemate (both bridgehead hydrogen on same side of plane of the perhydroquinoline ring rather than on opposite sides as in I or II). The trans-(−)-enantiomer (II) is one of the two stereoisomers represented by I and has most if not all the dopaminergic activity of the racemate, including the ability to treat sexual dysfunction and impotence.

The above compounds contain two basic groups, the alkylated hexahydroquinoline ring nitrogen and the 2-amino group on the pyrimidino ring. (Both ring nitrogens are acidic.) The hexahydroquinoline ring nitrogen is the more basic of the two and forms acid addition salts readily. Strong inorganic acids such as the mineral acids or strong organic acids such as p-toluenesulfonic acid, can form di salts when employed in excess. Pharmaceutically-acceptable acid addition salts of the compounds represented by I or II above thus include mono or di salts derived from inorganic acids such as: hydrochloric acid, nitric acid, phosphoric acid, sulfuric acid, hydrobromic acid, hydriodic acid, phosphorous acid and the like, as well as salts derived from organic acids such as aliphatic mono and dicarboxylic acids, phenyl-substituted alkanoic acids, hydroxyalkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, α-hydroxybutyrate, glycollate, malate, tartrate, methanesulfonate, propanesulfonate, naphthalene-1-sulfonate, naphthalene-2-sulfonate and the like salts.

The compounds of this invention are prepared according to the procedures set forth in the copending application of Nichols and Kornfeld, Ser. No. 535,503, filed this even day. Generally speaking, to prepare these derivatives, one starts with a trans-(±)-1-C$_1$–C$_3$ alkyl or allyl-6-oxodecahydroquinoline which is reacted with dimethylamino formamide dimethylacetal to yield the corresponding 7-dimethylaminomethylene derivative, ring closure of which with guanidine, or a guanidine substituted with one or two, same or different, alkyl groups such as methyl, ethyl and n-propyl yields a trans-(±) compound of Formula I wherein R$^1$ is NH$_2$, NHR$^3$ or NH$^4$R$^5$, wherein R$^3$ is methyl, ethyl or n-propyl, R$^2$ is H and R, R$^4$ and R$^5$ have their previous meanings. If it is desired to prepare the trans-(−)-isomer II, the same chemistry is involved but the starting ketone is a trans-(−)-isomer prepared by resolution of the trans-(±)-racemate by the method of Schaus and Booher, Ser. No. 439,107, filed Nov. 1, 1982. Compounds according to formula I or II wherein R$^1$ is NHR$^3$ and R$^3$ is C$_1$–C$_3$ alkyl-CO or permissibly-substituted phenyl-CO are prepared by acylation of a compound in which R$^1$ ia NH$_2$.

Compounds according to Formulas I and II wherein R$^2$ is other than H are prepared, where R$^2$ is CH$_3$, by reacting, for example, guanidine with trans-(±) or trans-(−)-1-alkyl or allyl6-oxo-7-acetyldecahydroquinoline. These intermediates are prepared by the procedure of Schaus, Huser and Booher, Ser. No. 535,519, filed this even day. Where R$^2$ is Cl or Br, a different intermediate, a trans-(±)- or trans-(−)-1-alkyl or allyl-6-oxo-7-alkoxycarbonyldecahydroquinoline is used, also prepared also by method of Schaus, Huser and Booher, (loc. cit.). Condensation of such an intermediate with guanidine, an N-alkyl guanidine or an N,N-dialkylguanidine yields a trans-(±)- or trans-(−)-2-amino-4-hydroxy-6-alkyl or allyl-5,5a,6,7,8,9,9a,10-octahydropyrimido[4,5-g]quinoline, reaction of which with PBr$_3$, POCl$_3$ and the like yields the desired 4-halo derivative.

The starting material, a 1-substituted-6-oxodecahydroquinoline when the N-1 substituent is C$_1$—C$_3$ alkyl, can be prepared by the method of U.S. Pat. No.

4,198,415, columns 4–5. Preferably, however, the method of Schaus, Ser. No. 384,817, filed June 2, 1982, is employed. If the N-1 substituent is to be allyl, the trans-(±)-1-alkyl-6-oxodecahydroquinoline is reacted with CNBr or an alkyl chloroformate to yield an intermediate N-cyano or N-carbamoyl derivative. Hydrolysis of the cyano or carbamate group yields the secondary amine which can be alkylated and the N-allyl compound cyclized as before. This procedure is more fully exemplified in the copending application of Titus and Bach, Ser. No. 535,522, filed this even day.

The preparation of compounds represented by I or II above is more specifically described in the following examples.

EXAMPLE 1

Preparation of trans-(±)-2-amino-6-methyl-5,5a,6,7,8,9,9a,10-octahydropyrimido[4,5-g]quinoline A reaction mixture was prepared from 1.8 g. of trans-(±)-1-methyl-6-oxodecahydroquinoline and 2.2 g. of tris-dimethylaminomethane in 18 ml. of toluene. The reaction mixture was refluxed under nitrogen for about 12 hours. An additional 0.8 g. of tris-dimethylaminomethane were added and refluxing continued under nitrogen for an additional 5 hours. The reaction mixture was then concentrated to dryness in vacuo. The resulting residue containing trans(±)-1-methyl-6-oxo-7-(dimethylaminomethylene)decahydroquinoline formed in the above reaction was dissolved in 40 ml. of ethanol to which was added 1.5 g. of guanidine carbonate. The resulting mixture was heated overnight to reflux temperature under a nitrogen atmosphere. On cooling, a crystalline precipitate formed which was collected by filtration and the filter cake washed with ethanol; yield=0.68 g. of a light yellow powder. The material was dissolved in 1N aqueous hydrochloric acid. The acidic solution was then made basic with 10% aqueous sodium hydroxide. Trans-(±)-2-amino-6-methyl-5,5a,6,7,8,9,9a,10-octahydropyrimido[4,5-g]quinoline free base, being insoluble in the alkaline layer, separated and was extracted with chloroform. The chloroform extract was dried and the chloroform removed in vacuo. The residue, comprising trans-(±)-2-amino-6-methyl-5,5a,6,7,8,9,9a,10-octahydropyrimido[4,5-g]quinoline was suspended in ethanol and the ethanol solution saturated with gaseous hydrogen chloride. The solvent was removed in vacuo and the resulting residue, the dihydrochloride salt of trans-(±)-2-amino-6-methyl-5,5a,6,7,8,9,9a,10-octahydropyrimido[4,5-g]quinoline, was recrystallized from hot ethanol. Sixty-six mg. of dihydrochloride salt were obtained having the following analysis (after drying at 150° C.):

Theory: C, 49.49; H, 6.92; N, 19.24.
Found: C, 49.61; H, 7.03; N, 18.92.

The higher temperature drying was necessary because it became apparent after drying at lower temperatures that the dihydrochloride salt crystallizes as a solvate and the solvent must be removed by drying to obtain a reproducible analysis.

The above reaction was repeated except that 1 g. of trans-(±)-1-n-propyl-6-oxo-7-dimethylaminomethylenedecahydroquinoline was reacted with 0.4 g. of guanidine carbonate in 20 ml. of anhydrous ethanol. (Trans-(±)-1-n-propyl-6-oxo-7-dimethylaminomethylenedecahydroquinoline was prepared from trans-(±)-1-n-propyl-6-oxodecahydroquinoline and tris-dimethylaminomethane according to the above procedure). The reaction mixture was heated under reflux temperature overnight at which time a precipitate was observed. The reaction mixture was chilled in an ice bath and a light yellow crystalline precipitate comprising trans-(±)-2-amino-6-n-propyl-5,5a,6,7,8,9,9a,10-octahydropyrimido[4,5-g]quinoline formed in the above reaction was collected. The filter cake was washed with ethanol and then dried; mp.=above 260° C.

Analysis calculated: C, 68.26; H, 9.00; N, 22.74.
Found: C, 68.45; H, 8.87; N, 22.26.

Trans-(±)-2-amino-6-n-propyl-5,5a,6,7,8,9,9a,10-octahydropyrimido[4,5]quinoline was dissolved in 1N aqueous hydrochloric acid and the acidic solution extracted with ether. The acidic solution was then made basic with 10% aqueous sodium hydroxide. Trans-(±)-2-amino-6-n-propyl-5,5a,6,7,8,9,9a,10-octahydropyrimido[4,5-g]quinoline precipitated and was separated by filtration. Six-tenths grams of trans-(±)-2-amino-6-n-propyl-5,5a,6,7,8,9,9a,20-octahydropyrimido[4,5-g]quinoline were obtained. The free base was again dissolved in 1N aqueous hydrochloric acid, and the water removed in vacuo. The resulting residue was recrystallized from hot ethanol. Trans-(±)-2-amino-6-n-propyl-5,5a,6,7,8,9,9a,10-octahydropyrimido[4,5-g]quinoline dihydrochloride thus prepared had the following analysis.

Analysis calculated for $C_{14}H_{22}N_4.2HCl.H_2O$:
C, 49.74; H, 7.75; N, 16.57;
Cl, 20.97;
Found: C, 49.88; H, 8.03; N, 16.81;
Cl, 20.87.

After drying at 120° C., analysis indicated that water of hydration and one-half mole of hydrogen chloride had been lost to yield trans-(±)-2-amino-6-n-propyl-5,5a,6,7,8,9,9a,10-octahydropyrimido-[4,5-g]quinoline sesquihydrochloride having the following analysis.

Analysis calculated for $C_{14}H_{22}N_4.1.5\ HCl$:
C, 55.86; H, 7.87; N, 18.61;
Cl, 17.03.
Found: C, 55.49; H, 7.83; N, 18.35;
Cl, 17.03.

EXAMPLE 2

Preparation of Trans-(±)-2-acetylamino-6-n-propyl-5,5a,6,7,8,9,9a,10-octahydropyrimido[4,5-g]quinoline A solution was prepared containing 0.75 g of trans-(±)-2-amino-6-n-propyl-5,5a,6,7,8,9,9a,10-octahydropyrimido[4,5-g]quinoline in 20 ml. of pyridine and 0.34 g. of acetic anhydride was added thereto in dropwise fashion. The reaction mixture was heated to reflux temperature under a nitrogen blanket overnight. TLC at this point in time indicated that starting material was still present; therefore, about 1.5 ml. more acetic anhydride were added and the reaction mixture again heated to reflux temperature under a nitrogen blanket. TLC, using a 9:1 chloroform/methanol solvent system containing ammonia, indicated that the reaction had gone largely toward completion but that some starting material was still present. The reaction mixture was therefore concentrated in vacuo and the resulting residue triturated in hot ethyl acetate. On cooling, crystals formed which were isolated by filtration. Thirty-four hundredths grams of trans-(±)-2-acetyl amino-6-n-propyl-5,5a,6,7,8,9,9a,10-octahydropyrimido[4,5-g]quinoline were obtained; molecular ion at 288; nmr and infrared spectra were in conformance with the proposed structure.

Following the above procedure, trans-(±)-2-amino-6-n-propyl-5,5a,6,7,8,9,9a,10-octahydropyrimido[4,5-g]quinoline was reacted with benzoyl chloride in pyridine solution. The residue obtained after working up the reaction mixture as indicated above was chromatographed over florisil using chloroform with increasing amounts (0–10%) of methanol as the eluant. Fraction ten contained the desired 2-benzoylamino compound (by TLC). The solvent was removed therefrom in vacuo. The resulting residue was dissolved in ethanol and gaseous hydrogen chloride passed into the ethanol solution. Addition of ether to the point of incipient precipitation yielded trans-(±)-2-benzoylamino-6-n-propyl-5,5a,6,7,8,9,9a,10-octahydropyrimido[4,5-g]quinoline dihydrochloride; molecular ion at 350.

Analysis (after drying at 130° C.):
C, 59.57; H, 6.67; N, 13.23.
Found: C, 59.35; H, 6.85; N, 12.99.

EXAMPLE 3

Preparation of
5aR,9aR-2-Amino-6-n-propyl-5,5a,6,7,8,9,9a,10-octahydropyrimido[4,5-g]quinoline Following the procedure of Example 1, 4aR,8aR-1-n-propyl-6-oxo-7-dimethylaminomethylenedecahydroquinoline (prepared from 4aR,8aR-1-n-propyl-6-oxodecahydroquinoline and tris-dimethylaminomethane) was eacted with guanidine carbonate in anhydrous ethanol solution. The reaction was carried out and the reaction mixture worked up as in Example 1 to yield 2.4 g. of 5aR,9aR-2-amino-6-n-propyl-5,5a,6,7,8,9,,9a,10-octahydropyrimido[4,5-g]quinoline.

The product was suspended in ethanol and gaseous hydrogen chloride bubbled through the suspension. The resulting solution was evaporated to dryness in vacuo and the residual yellow oil dissolved in a small amount of ethanol (about 10 cc). Ether was added to the point of incipient precipitation and the mixture heated on the steam bath. Upon cooling, fine, powdery crystals formed which were separated by filtration. The filter cake was washed with ethanol to yield 0.72 g. of the dihydrochloride salt of 5aR,9aR-2-amino-6-n-propyl-5,5a,6,7,8,9,9a,10-octahydropyrimido[4,5-g]quinoline.

Analysis (after drying at 180° C.):
C, 52.67; H, 7.58; N, 17.55.
Found: C, 52.81; H, 7.75; N, 17.65.
Molecular ion at 246;
Optical rotation $[\alpha]589°$ 25° C. = −99.6°;
$[\alpha]360°$ 25° C. = −374.8°.

EXAMPLE 4

Preparation
Trans-(±)-2-dimethylamino-6-n-propyl-5,5a,6,7,8,9,,9a,10-octahydropyrimido[4,5-g]quinoline A reaction mixture was prepared from 4.7 g. of trans-(±)-1-n-propyl-6-oxo-7-dimethylaminomethylenedecahydroquinoline and 2.5 g. of 1,1-dimethylguanidinehydrochloride in 50 ml. of anhydrous ethanol. The reaction mixture was heated overnight under a nitrogen atmosphere, and was then cooled and the volatile constituents removed in vacuo. The resulting residue was dissolved in ethyl acetate and the ethyl acetate solution contacted with an excess of 10% aqueous sodium hydroxide. Trans-(±)-2-dimethylamino-6-n-propyl-5,5a,6,7,8,9,9a,10-octahydropyrimido[4,5-g]quinoline formed in the above reaction, being insoluble in the basic layer, remained in the ethyl acetate layer. The aqueous layer was separated and the ethyl acetate layer extracted once with water and once with saturated aqueous sodium chloride. The ethyl acetate layer was dried and the ethyl acetate removed in vacuo to leave 0.75 g. of an orange oil. The oily residue was chromatographed over florisil using hexane containing increasing amounts (1–50%) of ethyl acetate as the eluant. Fractions shown by TLC to contain the desired trans-(±)-2-dimethylamino-6-n-propyl-5,5a,6,7,8,9,9a,10-octahydropyrimido[4,5-g]quinoline were combined and the solvent removed from the combined fractions in vacuo. The resulting residue was dissolved in ethanol and gaseous hydrogen chloride passed into the solution thus forming the corresponding dihydrochloride salt. The ethanol was removed therefrom in vacuo and the dihydrochloride salt crystallized from a methanol ethyl acetate solvent mixture to yield 0.170 g. of a white solid having a molecular ion at 274.

Analysis calculated: C, 55.33; H, 8.13; N, 16.13.
Found: C, 55.67; H, 8.19; N, 16.19.

Following the above procedure, but substituting N-methylguanidine for N,N-dimethylguanidine, trans-(±)-2-methylamino-6-n-propyl-5,5a,6,7,8,9,9a,10-octahydropyrimido[4,5-g]quinoline was prepared. The compound was purified by chromatography over florisil using methylene dichloride containing increasing (0–10%) methanol as the eluant; yield=0.66 g. The monohydrochloride salt was prepared by adding an equivalent of 0.1N hydrochloric acid to the solid and recrystallizing the product from methanol; yield=599 mg.

Analysis calculated: C, 60.69; H, 8.49; N, 18.87;
Cl, 11.94.
Found: C, 60.96; H, 8.53; N, 19.07;
Cl, 11.74.

In Examples 1–2 and 4, the optically active 5aR,9aR derivative can be prepared from the desired 4aR,8aR-1-$C_{1-3}$-alkyl-6-oxo-7-dimethylaminomethylene decahydroquinoline and a suitable guanidine.

EXAMPLE 5

Preparation of
trans-(±)-2-Amino-4-methyl-6-n-propyl-5,5a,6,7,8,9,,9a,10-octahydropyrimido[4,5-g]quinoline Following the procedures of Schaus, Huser, and Booher, (loc. cit) a reaction mixture was prepared by adding 13.7 ml. of 1.6M n-butyllithium in hexane to a solution containing 3.1 ml. of diisopropylamine and 22 ml. of THF at about 0° C. under a nitrogen atmosphere. The reaction mixture was stirred for about 30 minutes. Next, 2.0 g. of trans-(±)-1-n-propyl-6-oxodecahydroquinoline in a small amount of THF was added while containing the reaction mixture at about −78° C. The solution was stirred for two hours at which time 1.1 ml. of acetyl chloride was added. This new reaction mixture was stirred at about −78° C. for about 30 minutes and then at room temperature for two hours. The reaction mixture was next poured into water and the consequent aqueous mixture acidified to a pH=9–10 with 1N aqueous hydrochloride acid. The aqueous solution was extracted three times with equal volumes of methylene dichloride. The methylene dichloride extracts were combined and the combined extracts dried. Evaporation of the solvent yielded 2.7 g. of trans-(±)-1-n-propyl-6-oxo-7-acetyldecahydroquinoline. The crude reaction product (without further purification) was mixed with about 0.9 g. of guanidine carbonate. Forty ml. of ethanol were added and the reaction mixture refluxed under a nitrogen atmosphere. The reaction mixture was then evaporated to dryness and the crude product chromatographed over florisil. Fractions shown to contain trans-(±)-2-amino-4-methyl-6-n-propyl-5,5a,6,7,8,9-,9a,10-octahydropyrimido[4,5-g]quinoline formed in the above reaction were combined to yield 270 mg of free base, 10 ml. of 0.1N aqueous hydrochloric acid were added thereto. The hydrochloride salt thus formed was recrystallized from ethanol; m.p.=above 240° C.; mass spectrum molecular ion at 260, small peak at 268.

Analysis Calculated: C, 54.05; H, 7.86; N, 16.81;
Found: C, 53.93; H, 7.98; N, 16.61.

EXAMPLE 6

Preparation of trans-(±)-2-Amino-4-chloro-6-n-propyl-5,5a,6,7,8,9-,9a 10-octahydropyrimido[4,5-g]quinoline A reaction mixture was prepared from 2.0 g. of trans-(±)-1-n-propyl-6-oxo-7-ethoxycarbonyldecahydro quinoline (prepared by the method of Schaus, Huser, and Booher—loc. cit.), 20 ml. of anhydrous ethanol at 0.67 g. of guanidine carbonate. The reaction mixture was heated to reflux temperature overnight under a nitrogen atmosphere. The white precipitate which formed was collected by filtration and the filter cake washed with ethanol and dried; yield=1.36 g. The filter cake was dissolved in 52 ml. of 0.1N aqueous hydrochloric acid. The acidic mixture was filtered and the filtrate concentrated in vacuo. The solid residue was dissolved in boiling methanol. The methanol solution was filtered and trans-(±)-2-amino-4-hydroxy-6-n-propyl-5,5a,6,7,8,9,9a,10-octahydropyrimido[4,5-g]quinoline hydrochloride thus prepared crystallized to yield 0.79 g. of product. The free base had the following physical characteristics: mass spectrum, molecular ion at 262.

Analysis Calculated: C, 64.08; H, 8.45; N, 21.36;
Found: C, 64.18; H, 8.51; N, 21.13.

The hydrochloride salt had the following physical characteristics: mass spectrum, molecular ion at 262.

The 4-hydroxy product thus obtained was refluxed with 4 ml. of phosphorous oxychloride. The reaction mixture, containing trans-(±)-2-amino-4-chloro-6-n-propyl-5,5a,6,7,8,9,9a,10-octahydropyrimido[4,5-g]-quinoline formed in the above reaction, was poured onto ice and the resulting aqueous mixture made basic. The basic mixture was filtered and the insoluble material dissolved in 0.1N aqueous hydrochloric acid. The hydrochloride salt thus prepared was recrystallized from ethanol to yield trans-(±)-2-amino-4-chloro-6-n-propyl-5,5a,6,7,8,9,9a,10-octahydropyrimido[4,5-g]quinoline hydrochloride having the following physical characteristics. Mass spectrum, molecular ion at 280, smaller peak at 282.

Analysis Calculated: C, 53.00; H, 6.99; N, 17.66;
Found: C, 53.15; H, 6.92; N, 17.77.

The above procedures provide either the free base or a hydrochloride salt. If it is desired to prepare a new salt, a solution containing one equivalent of a second non-toxic acid can then be added to a solution of the free base, and the salt isolated by filtration or evaporation. Alternatively, the solvent can be removed from the dried organic extract and the free base obtained as a residue. The free base can then be dissolved in a suitable solvent and a different non-toxic acid added as a solution. The preferred salt for use in the novel processes and formulations of this invention is the mono HCl salt. It can be prepared, for example, by adding an equivalent of ethanolic hydrogen chloride to an ethanol solution of the free base, followed by evaporation of the ethanol and recrystallization of the salt. If it is desired to make a disalt such as a dihydrochloride salt, HCl gas can be passed into a solution of the free base to the point of saturation and the di HCl salt isolated by filtration.

The free base can readily be prepared by dissolving a salt in water and then adding an excess of an aqueous base. The octahydropyrimido[4,5-g]quinoline, being insoluble in the basic layer, is extracted into a water-immiscible organic solvent. The organic extract is separated and dried and the free base obtained as a residue after evaporation of the solvent.

The ability of a trans-(±) or trans-(−)-2-amino-4-permissibly-substituted-6-alkyl(or allyl)-octahydropyrimido[4,5-g]quinoline or a salt thereof to affect sexual behavior in male mammals is illustrated by the following experiment:

Male rats that required at least 5 minutes to achieve ejaculation were used. The behavioral tests were initiated with the introduction of a sexually receptive female rat into the behavioral arena and were stopped immediately following the first mount after ejaculation. The following behavioral indicies were measured:

| BEHAVIORAL INDEX | DEFINITION |
| --- | --- |
| 1. Mount Latency (ML): | Time from introduction of female to the first mount |
| 2. Intromission Latency (IL): | Time from introduction of female to the first intromission |
| 3. Ejaculatory Latency (EL): | Time interval from intromission to ejaculation |
| 4. Postejaculatory Interval (PEI): | Time interval from ejaculation to next mount |
| 5. Mount Frequency (MF): | Total number of mounts required to achieve ejaculation |
| 6. Intromission Frequency (IF): | Total number of mounts with intromission required to achieve ejaculation |

Each male rat was given a solution containing either the vehicle alone (1 millimolar acetic acid plus 1 millimolar ascorbic acid) in water or trans-(−)-2-amino-6-n-propyl-5,5a,6,7,8,9,9a,10-octahydropyrimido[4,5-g]quinoline dihydrochloride at 25 mcg./kg. in the same vehicle by subcutaneous injection 30 minutes prior to behavioral testing. One week after the drug test, the vehicle alone was retested.

The results of the above experiment are given in Table I below. In the Table, column 1 gives the treatment, and columns 2–7 the behavioral indices (x±SE for 9 rats) for each treatment in column 1.

TABLE I

| Treatment | ML* | IL* | EL* | PEI* | MF** | IF** |
| --- | --- | --- | --- | --- | --- | --- |
| Vehicle (Before) | 85.0 ± 30.8 | 162.0 ± 55.2 | 708.0 ± 131.2 | 351.1 ± 24.6 | 19.0 ± 1.9 | 8.4 ± 1.3 |
| Drug | 19.0 ± | 46.8 ± | 326.0 ± | 347 ± | 11.7 ± | 5.4 ± |

TABLE I-continued

| Treatment | ML* | IL* | EL* | PEI* | MF** | IF** |
|---|---|---|---|---|---|---|
| (25 mcg/kg s.c.) | 6.4 | 15.6 | 68.9 | 44.2 | 0.2 | 0.4 |
| Vehicle (After) | 122.6 ± 56.6 | 144.8 ± 62.5 | 640.0 ± 63.0 | 343.4 ± 21.1 | 21.1 ± 3.7 | 5.7 ± 0.9 |

*ML, IL, EL and PEI values are expressed in seconds.
**MF and IF values are expressed in number of mounts.

A repeat run at 0.25 mcg. was carried out with the following results (Table II)(values represent x+SE for 11 rats).

TABLE II

| Treatment | ML | IL | EL | PEI | MF | IF |
|---|---|---|---|---|---|---|
| Vehicle (Before) | 21.1 ± 5.4 | 64.5 ± 11.9 | 942.9 ± 86.9 | 329.5 ± 3.5 | 28.2 ± 3.5 | 9.3 ± 1.4 |
| Drug | 13.6 ± 7.4 | 38.1 ± 10.3 | 398.8 ± 58.6 | 310.3 ± 24.7 | 18.1 ± 2.1 | 7.7 ± 0.8 |
| Vehicle After | 12.4 ± 2.7 | 37.4 ± 14.2 | 523.2 ± 116.2 | 298.5 ± 17.9 | 23.1 ± 2.9 | 11.1 ± 1.5 |

According to the data presented in Table I, the drug produced statistically significant improvements in ejaculatory latency (EL) and mount frequency (MF) compared to either pre- or postcompound vehicle treatments and in intromission latency (IL) compared to prior vehicle treatment. These data are indicative of dramatic improvements in sexual performance specifically related to the effects of the drug. According to the data presented in Table II, a single subcutaneous dose of drug of 250 ng/Kg produced statistically significant improvements in ejaculatory latency (EL) compared to prior vehicle treatment. Although there were no statistically significant differences in the comparison of the mean performance values between drug and subsequent vehicle responses, it is important to note that 6 of 11 rats showed better performance in each performance index following drug treating compared to the subsequent vehicle treatment, 9 and 8 of the 11 rats showed improvements in mount frequency and intromission frequency, respectively. These data are supportive of the view that trans-(−)-2-amino-6-n-propyl-5,5a,6,7,8,9,9a,10-octahydropyrimido[4,5-g]quinoline dihydrochloride has behavioral effects in doses as low as 250 ng/Kg. Similar behavior experiments were conducted using drug doses of 2.5 ng/Kg, s.c., but no behavioral effects were observed.

The effects of trans-(−)-2-amino-6-n-propyl-5,5a,6,7,8,9,9a,10-octahydropyrimido[4,5-g]quinoline dihydrochloride on male rat sexual behavior were also evaluated in rats that showed no mating behavior or were unable to achieve ejaculation in the 30 minute test period. The effects of 25 mcg/Kg, s.c. of drug on the mating performance of these animals are summarized in Table III. The drug appeared to have the capacity to initiate sexual behavior in animals that showed no prior sexual behavior and to amplify sexual behavior in animals that were unable to achieve ejaculation. The mating performance of rats from these groups that were able to achieve ejaculation after drug treatment and subsequent vehicle treatments were evaluated. These animals showed a significant reduction in the number of mounts required for ejaculation (mount frequency) with drug treatment compared to vehicle treatment.

TABLE III

EFFECT OF A SINGLE ADMINISTRATION OF DRUG (25 MCG/KG, S.C.) ON MATING PERFORMANCE OF IMPOTENT RATS

| PERCENTAGE OF RATS DISPLAYING MATING BEHAVIOR | |
|---|---|
| Vehicle (1 week prior) | 0.0% (0/8) |
| Drug | 87.5% (7/8) |
| Vehicle (1 week after) | 37.5% (3/8) |
| PERCENTAGE OF RATS ABLE TO ACHIEVE EJACULATION IN 30 MIN. | |
| Vehicle (before) | 0.0% (0/14) |
| Drug | 92.9% (13/14) |
| Vehicle (after) | 50.0% (7/14) |

| ACTIVITY OF MALES ACHIEVING EJACULATION | | | | | | |
|---|---|---|---|---|---|---|
| | ML | IL | EL | PEI | IF | MF |
| Drug (N = 7) | 34.4 ± 13.7 | 79.6 ± 42.3 | 298.4 ± 48.5 | 308.1 ± 36.9 | 4.9 ± 1.0 | 8.7 ± 1.0 |
| Post Vehicle (N = 7) | 50.3 ± 22.0 | 80.8 ± 31.6 | 537.1 ± 110.5 | 291.3 ± 26.1 | 6.1 ± 1.1 | 27.1* ± 3.9 |

*Significantly greater than drug (P<.003)

The effects of trans-(±)- and trans-(−)-2-amino-6-n-propyl-5,5a,6,7,8,9,9a,10-octahydropyrimido[4,5-g]quinoline dihydrochloride on sexual behavior of female mammals were evaluated in ovariectomized, estrogen-treated rats. The change in the lordosis-to-mount ratio was measured (increase in presenting by the female for mounting by a male per mount). The protocol of Foreman and Moss, *Physiology and Behavior*, 22, 283 (1979), was used. Table IV which follows gives the results of this experiment. In the Table, column 1 gives the name of the drug used, if any, column 2 the dose in mcg./kg. and column 3 the change in lordosis-to-mount ratio with standard error.

TABLE IV

| Treatment | Dose (mcg./kg.) | Change in Lordosis-to-Mount Ratio (x ± SE) |
|---|---|---|
| Vehicle | | .158 ± .042 |
| Trans-(±)-Racemate | 25 | .580 ± .063* |
| Trans-(−)-Stereoisomer | 25 | .760 ± .058** |

*Significantly greater than vehicle P < .05
**Significantly greater than trans-(±) P < .05

A similar experiment was carried out on the two stereoisomers; trans-(−)-2-amino-6-n-propyl-5,5a,6,7,8,9,9a,10-octahydropyrimido[4,5-g]quinoline and the trans-(+)-isomer. Response to the trans-(+)-isomer was not significantly greater than the response to vehicle alone (0.093±0.063 to 0.035±0.018) whereas the trans-(−)-isomer gave a highly significant change 0.753±0.031.

Table V below gives the effect of a series of dose levels of trans-(−)-2-amino-6-n-propyl-5,5a,6,7,8,9,9a,10-octahydropyrimido[4,5-g]quinoline on the lordosis-to-mount ratio in ovariectomized, estrogen-treated rats.

TABLE V

| Dosage mcg./kg. | Change In Lordosis-To-Mount Ratio** |
|---|---|
| 0 | .074 ± .025 |
| 2.5 | .284 ± .064 |
| 7.5 | .405 ± .083 |
| 25 | .786 ± .028 |

**All values are X ± s.c. for 19 animals.
Behavioral response to vehicle was significantly lower (P < .01) than response to drug at each dosage.

In carrying out my novel therapeutic processes, a pharmaceutically-acceptable salt of a compound according to I or II formed with a non-toxic acid such as hydrochloric acid is conveniently administered orally or parenterally to a mammal suffering from a sexual dysfunction or in need of sexual potentiation. For parenteral administration, a water soluble salt of the drug, a hydrochloride salt, for example, is dissolved in an isotonic salt solution and administered by the iv route. Dose levels of from 0.25–25 mcg./kg. of mammalian weight are found to be effective to improve sexual function. For oral administration, a pharmaceutically-acceptable salt of the drug is mixed with standard pharmaceutical excipients such as starch and loaded into capsules, each containing 0.1-15 mg. of active drug. Dosage levels of from 0.1-100 mcg./kg. have been found to be effective in improving sexual function, particularly in increasing male potency. The oral dosage forms would be administered 3–4 times per day, giving a daily dosage range of about 0.3 to about 400 mcg./kg. per day.

Other oral dosage forms, suspension, elixers and tablets, can also be utilized and are preparable by standard procedures.

I claim:

1. A method for treating sexual dysfunction in mammals suffering from such dysfunction and in need of treatment which comprises administering to said mamals an effective dose of a trans-(±)-racemate of the formula

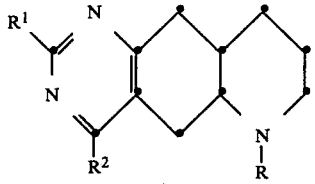

or of a stereoisomer thereof of the formula

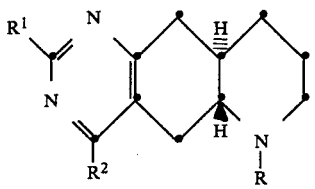

wherein R is $C_1$–$C_3$ alkyl or allyl, $R^1$ is $NH_2$, $NHR^3$ or $NR^4R^5$ and $R^2$ is H, Cl, Br or $CH_3$; wherein $R^3$ is methyl, ethyl, n-propyl, $C_1$–$C_3$ alkyl-CO, phenyl-CO or substituted phenyl-CO wherein said substituents are 1 or 2 members of the group; Cl, F, Br, $CH_3$, $C_2H_5$, $CH_3O$, $C_2H_5O$ and $CF_3$; and $R^4$ and $R^5$ are individually methyl, ethyl or n-propyl; and pharmaceutically acceptable acid addition salts thereof.

2. A method according to claim 1 in which trans-(±)-2-amino-6-n-propyl-5,5a,6,7,8,9,9a,10-octahydropyrimido[4,5-g]quinoline is administered.

3. A method according to claim 1 in which trans-(−)-2-amino-6-n-propyl-5,5a,6,7,8,9,9a,10-octahydropyrimido[4,5-g]quinoline is administered.

4. A method according to claim 1 in which trans-(−)-2-amino-6-n-propyl-5,5a,6,7,8,9,9a,10-octahydropyrimido[4,5-g]quinoline dihydrochloride is administered.

5. A method according to claim 1 in which a male mammal is treated.

6. A method according to claim 1 in which a female mammal is treated.

7. A method of restoring potency in impotent male mammals in need of treatment which comprises administering to such impotent male mammals a potency restoring dose of a trans-(±)-racemate of the formula

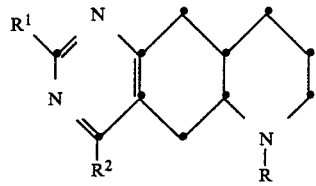

or of a stereoisomer thereof of the formula

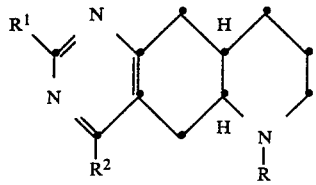

wherein R is $C_1$–$C_3$ alkyl or allyl, $R^1$ is $NH_2$, $NHR^3$ or $NR^4R^5$ and $R^2$ is H, Cl, Br or $CH_3$; wherein $R^3$ is methyl, ethyl, n-propyl, $C_1$–$C_3$ alkyl-CO, phenyl-CO, or substituted phenyl-CO wherein said substituents are 1 or 2 members of the group; Cl, F, Br, $CH_3$, $C_2H_5$, $CH_3O$, $C_2H_5O$ and $CF_3$; and $R^4$ and $R^5$ are individually methyl, ethyl or n-propyl; and pharmaceutically-acceptable acid addition salts thereof.

8. A method according to claim 7 in which trans-(±)-2-amino-6-n-propyl-5,5a,6,7,8,9,9a,10-octahydropyrimido[4,5-g]quinoline is administered.

9. A method according to claim 7 in which trans-(−)-2-amino-6-n-propyl-5,5a,6,7,8,9,9a,10-octahydropyrimidol[4,5-g]quinoline is administered.

10. A method according to claim 7 in which trans-(−)-2-amino-6-n-propyl-5,5a,6,7,8,9,9a,10-octahydropyrimido[4,5-g]quinoline dihydrochloride is administered.

* * * * *